United States Patent [19]

Vogt et al.

[11] Patent Number: 5,656,361
[45] Date of Patent: Aug. 12, 1997

[54] MULTIPLE APPLICATION MELTBLOWN NONWOVEN WET WIPE AND METHOD

[75] Inventors: Clifford Marshall Vogt, Roswell; Bernard Cohen, Berkeley Lake; Clifford Jackson Ellis, Woodstock, all of Ga.

[73] Assignee: Kimberly-Clark Worldwide, Inc., Neenah, Wis.

[21] Appl. No.: 686,227

[22] Filed: Jul. 23, 1996

[51] Int. Cl.$^6$ .......................... A01N 25/08; A61L 15/42; B32B 27/02; B32B 27/06
[52] U.S. Cl. .................. 428/198; 15/104.93; 424/402; 424/404; 442/60; 442/119; 442/123; 604/360; 427/429
[58] Field of Search ..................... 15/104.93; 424/402, 424/404; 442/60, 119, 123; 604/360; 428/198; 427/429

[56] References Cited

U.S. PATENT DOCUMENTS

| | | | |
|---|---|---|---|
| Re. 31,885 | 5/1985 | Meitner | 252/91 |
| Re. 32,514 | 10/1987 | Steklenski | 524/32 |
| D. 239,566 | 4/1976 | Vogt | D59/2 R |
| D. 264,512 | 5/1982 | Rogers | D59/2 B |
| 3,016,599 | 1/1962 | Perry, Jr. | 28/78 |
| 3,704,198 | 11/1972 | Prentice . | |
| 3,755,527 | 8/1973 | Keller et al. | 264/210 |
| 3,795,571 | 3/1974 | Prentice . | |
| 3,811,957 | 5/1974 | Buntin | 136/146 |
| 3,849,241 | 11/1974 | Butin et al. . | |
| 3,855,046 | 12/1974 | Hansen et al. . | |
| 3,973,068 | 8/1976 | Weber | 28/198 |
| 3,978,185 | 8/1976 | Buntin et al. | 264/93 |
| 4,041,203 | 8/1977 | Brock et al. | 428/157 |
| 4,100,324 | 7/1978 | Anderson et al. | 428/288 |
| 4,118,531 | 10/1978 | Hauser | 428/224 |
| 4,196,245 | 4/1980 | Kitson et al. | 428/198 |
| 4,298,649 | 11/1981 | Meitner | 428/198 |
| 4,307,143 | 12/1981 | Meitner | 252/91 |
| 4,328,279 | 5/1982 | Meitner et al. | 428/289 |
| 4,426,417 | 1/1984 | Meitner et al. | 428/195 |
| 4,436,780 | 3/1984 | Hotchkiss et al. | 428/198 |
| 4,493,868 | 1/1985 | Meitner | 428/171 |
| 4,578,414 | 3/1986 | Sawyer et al. | 524/310 |
| 4,587,154 | 5/1986 | Hotchkiss et al. | 428/195 |
| 4,659,777 | 4/1987 | Riffle et al. | 525/100 |
| 4,663,220 | 5/1987 | Wisneski et al. | 428/22 |
| 4,689,362 | 8/1987 | Dexter | 524/266 |
| 4,698,388 | 10/1987 | Ohmura et al. | 525/88 |
| 4,745,142 | 5/1988 | Ohwaki et al. | 524/87 |

FOREIGN PATENT DOCUMENTS

| | | |
|---|---|---|
| 1049682 | 2/1979 | Canada . |
| 0205242 | 12/1986 | European Pat. Off. . |
| 0343304 | 11/1989 | European Pat. Off. . |

OTHER PUBLICATIONS

"Superfine Thermoplastic Fibers" by V. A. Wente, Industrial and Engineering Chemistry, vol. 48, No. 8, pp. 1342–1346 (1956).

"Manufacture of Superfine Organic Fibers", V. A. Wente et al., Navy Research Laboratory, Washington, D.C., NRL Report 4364 (111437), May 25, 1994, US Dept. of Commerce, Office of Technical Services.

"Melt Blowing—A One-Step Web Process for New Nonwoven Products" by R. R. Butin et al., Journal of the Technical Association of the Pulp and Paper Industry, vol. 56, No. 4, pp. 74–77 (1973).

"Surfactants and Detersive Systems", Encyclopedia of Chemical Technology, vol. 22, 3rd Ed., pp. 347–386.

"Cosmetics", Encyclopedia of Chemical Technology, Vo. 7, 4th Ed., pp. 580–603.

"Disinfectants and Antiseptics", vol. 8, pp. 237–292.

*Primary Examiner*—James C. Cannon
*Attorney, Agent, or Firm*—William E. Maycock

[57] ABSTRACT

A wet wipe which includes a pattern bonded polypropylene nonwoven web adapted to provide a sustained controlled release to a surface of an aqueous alcoholic composition contained within the nonwoven web. The nonwoven web has a basis weight of from about 17 to about 100 grams per square meter and includes polypropylene meltblown fibers having diameters in a range of from about 0.01 to about 50 micrometers. The aqueous alcoholic composition contained within the polypropylene nonwoven web is present in a range of from about 300 to about 600 weight percent, based on a dry weight of the nonwoven web of 34 grams per square meter. The wet wipe provides a first release of the aqueous alcoholic composition in a range of from about 40 to about 70 weight percent, a second release in a range of from about 10 to about 25 weight percent, and a third release in a range of from about 5 to about 18 weight percent, of the composition originally present in the nonwoven web. The total amount of the aqueous alcoholic composition remaining in the nonwoven web after three releases is no more than about 25 weight percent, based on the amount of the composition originally present. Also provided is a method of applying a sustained controlled release of an aqueous alcoholic composition to a surface.

16 Claims, No Drawings

MULTIPLE APPLICATION MELTBLOWN NONWOVEN WET WIPE AND METHOD

BACKGROUND OF THE INVENTION

The present invention relates to a wet wipe.

Wet wipes are well known, commercial consumer products which are available in many forms. Perhaps the most common form is a stack of individual, folded sheets packaged in a plastic container for use as baby wipes. Wet wipes also are available in individual, sealed packets which typically contain a single premoistened wipe and are useful for away-from-home cleaning needs. Although wet wipes frequently are based on cellulosic nonwoven sheets such as tissues, wet wipes which include a meltblown nonwoven web are known. However, wet wipes typically are used only once and then are discarded, regardless of the material of which they are made. Consequently, a wet wipe which may be used several times would be useful.

SUMMARY OF THE INVENTION

The present invention addresses some of the difficulties and problems discussed above by providing a wet wipe which may be used at least three times. Accordingly, the present invention provides a wet wipe which includes a pattern bonded polypropylene nonwoven web adapted to provide a sustained controlled release to a surface of an aqueous alcoholic composition contained within the nonwoven web. The nonwoven web has a basis weight of from about 17 to about 100 grams per square meter and includes polypropylene meltblown fibers having diameters in a range of from about 0.01 to about 50 micrometers. The aqueous alcoholic composition contained within the polypropylene nonwoven web is present in a range of from about 400 to about 600 weight percent, based on a dry weight of the nonwoven web of 34 grams per square meter. The wet wipe of the present invention provides a first release of the aqueous alcoholic composition in a range of from about 40 to about 70 weight percent, a second release in a range of from about 10 to about 25 weight percent, and a third release in a range of from about 5 to about 18 weight percent, all based on the amount of the composition originally present in the nonwoven web. The total amount of the aqueous alcoholic composition remaining in the nonwoven web after three releases is no more than about 25 weight percent, based on the amount of the composition originally present.

In certain embodiments, the polypropylene fibers may have diameters in a range of from about 0.1 to about 10 micrometers. In other embodiments, the polypropylene fibers may have diameters in a range of from about 15 to about 25 micrometers.

In general, the aqueous alcoholic composition may be any composition which contains both water and an alcohol. The alcohol, in turn, may be a saturated aliphatic alcohol having from one to about six carbon atoms. For example, the aqueous alcoholic composition may be an aqueous ethanol composition. As another example, the aqueous alcoholic composition may be an aqueous propanol composition. As a further example, the aqueous alcoholic composition may be an aqueous isopropanol composition.

The aqueous alcoholic composition also may contain disinfectants; antiseptics; surfactants, such as nonionic, anionic, cationic, and amphoteric surfactants; emollients; skin conditioners; antimicrobial agents, such as sterilants, sporicides, germicides, bactericides, fungicides, virucides, protozoacides, algicides, bacteriostats, fungistats, virustats, sanitizers, and antibiotics; and the like, by way of example only.

When the polypropylene meltblown fibers have diameters in a range of from about 0.1 to about 10 micrometers, the aqueous alcoholic composition contained within the polypropylene nonwoven web may be present in a range of from about 500 to about 600 weight percent, based on a dry weight of the nonwoven web of 34 grams per square meter. Moreover, the first release of the aqueous alcoholic composition may be in a range of from about 40 to about 55 weight percent of the composition originally present in the nonwoven web, the second release of the aqueous alcoholic composition may be in a range of from about 18 to about 23 weight percent of the composition originally present in the nonwoven web, and the third release of the aqueous alcoholic composition may be in a range of from about 12 to about 18 weight percent of the composition originally present in the nonwoven web. The total amount of the aqueous alcoholic composition remaining in the nonwoven web after three releases may be no more than about 25 weight percent of the composition originally present.

The present invention also provides a method of applying a sustained controlled release of an aqueous alcoholic composition to a surface. The method involves providing a pattern bonded polypropylene nonwoven web adapted to provide a sustained controlled release to a surface of an aqueous alcoholic composition contained within the nonwoven web, which nonwoven web has a basis weight of from about 17 to about 100 grams per square meter and includes polypropylene meltblown fibers having diameters in a range of from about 0.01 to about 50 micrometers. The nonwoven web is loaded with an aqueous alcoholic composition in an amount of from about 300 to about 600 weight percent, based on the dry weight of the nonwoven web. A surface is wiped a first time to release from about 40 to about 70 weight percent of the aqueous alcoholic composition in the nonwoven web, based on the amount of the aqueous alcoholic composition originally present in the nonwoven web. A surface is wiped a second time and a third time to release from about 10 about 25 weight percent of the aqueous alcoholic composition in the nonwoven web, and from about 5 to about 18 weight percent of the aqueous alcoholic composition in the nonwoven web, respectively, based on the amount of the aqueous alcoholic composition originally present in the nonwoven web. The total amount of the aqueous alcoholic composition remaining in the nonwoven web after three releases is no more than about 25 weight percent, based on the amount of the composition originally present in the nonwoven web.

As already described, the polypropylene meltblown fibers may have diameters in a range of from about 0.1 to about 10 micrometers or from about 15 to about 25 micrometers. Additionally, the aqueous alcoholic composition may be any composition which contains both water and an alcohol as stated earlier, and it also may contain disinfectants, antiseptics, surfactants, emollients, skin conditioners, and antimicrobial agents as noted above.

DETAILED DESCRIPTION OF THE INVENTION

Although the terms "wipe" and "wiper" are used synonymously in the art, the former term is preferred throughout this specification.

As used herein, the term "meltblown fibers" means fibers formed by extruding a molten thermoplastic material through a plurality of fine, usually circular, die capillaries as molten threads or filaments into converging high velocity gas (e.g. air) streams which attenuate the filaments of molten thermoplastic material to reduce their diameters. Thereafter, the meltblown fibers are carried by the high velocity gas stream and deposited on a collecting surface to form a web of randomly disbursed meltblown fibers. Meltblown fibers may be continuous or discontinuous and are generally tacky when deposited onto a collecting surface. Such fibers generally have an average diameter not greater than about 75 micrometers. For example, the average diameter may be in a range of from about 0.1 micrometers to about 50 micrometers.

The formation of fibers by meltblowing is well known in the art. See, by way of example, U.S. Pat. Nos. 3,016,599 to Perry, Jr., 3,704,198 to Prentice, 3,755,527 to Keller et al., 3,795,571 to Prentice, 3,811,957 to Buntin, 3,849,241 to Buntin et al., 3,978,185 to Buntin et al., 4,100,324 to Anderson et al., 4,118,531 to Hauser, and 4,663,220 to Wisneski et al. See, also, V. A. Wente, "Superfine Thermoplastic Fibers", *Industrial and Engineering Chemistry*, Vol. 48, No. 8, pp. 1342–1346 (1956); V. A. Wente et al., "Manufacture of Superfine Organic Fibers", Navy Research Laboratory, Washington, D.C., NRL Report 4364 (111437), dated May 25, 1954, United States Department of Commerce, Office of Technical Services; and Robert R. Buntin and Dwight T. Lohkamp, "Melt Blowing—A One-Step Web Process for New Nonwoven Products", *Journal of the Technical Association of the Pulp and Paper Industry*, Vol. 56, No.4, pp. 74–77 (1973).

The term "normalized" is used herein to indicate a value which has been converted to a value per unit basis weight, i.e., per osy, which is equivalent to 34 gsm. The normalized values are obtained by simply dividing each test result or experimental value by the basis weight in osy of the sample being tested. Because basis weights of nonwoven webs and similar materials may vary over a wide range, normalization was used to provide a basis for comparing results obtained with nonwoven webs having different basis weights.

As used herein, the term "pattern bonded" refers to a process of bonding a nonwoven web in a pattern by the application of heat and pressure. Pattern bonding typically is carded out at a temperature in a range of from about 80° C. to about 180° C. and a pressure in a range of from about 150 to about 1,000 pounds per linear inch (59–178 kg/cm). The pattern employed typically will have from about 10 to about 250 bonds/inch$^2$ (1–40 bonds/cm$^2$) covering from about 5 to about 30 percent of the wipe surface area. Such pattern bonding is accomplished in accordance with known procedures. See, for example, U.S. Design Pat. No. 239,566 to Vogt, U.S. Design Pat. No. 264,512 to Rogers, U.S. Pat. No. 3,855,046 to Hansen et al., and U.S. Pat. No. 4,493,868, supra, for illustrations of bonding patterns and a discussion of bonding procedures, which patents are incorporated herein by reference.

The term "aqueous alcoholic composition" is meant to encompass any composition which contains both water and an alcohol. The alcohol, in turn, may be a saturated aliphatic alcohol having from one to about six carbon atoms. By way of illustration, the alcohol may be methanol, ethanol, propanol, isopropanol, butanol, t-butanol, 2-butanol, pentanol, 2-pentanol, hexanol, 2,3-dimethyl-1-butanol, and the like, including mixtures of two or more alcohols. For example, the aqueous alcoholic composition may be an aqueous ethanol composition. As another example, the aqueous alcoholic composition may be an aqueous propanol composition. As a further example, the aqueous alcoholic composition may be an aqueous isopropanol composition. In general, the amount of alcohol present in the aqueous alcoholic composition may vary from about 1 to about 99 percent by volume. For example, the amount of alcohol present may be at least about 5 percent. As another example, the amount of alcohol present may be at least about 10 percent.

The aqueous alcoholic composition also may contain disinfectants; antiseptics; surfactants, such as nonionic, anionic, cationic, and amphoteric surfactants; emollients; skin conditioners; antimicrobial agents, such as sterilants, sporicides, germicides, bactericides, fungicides, virucides, protozoacides, algicides, bacteriostats, fungistats, virustats, sanitizers, and antibiotics; and the like, by way of example only.

In general, the nonwoven web will have a basis weight of from 17 to about 100 grams per square meter. For example, the basis weight may be in a range of from about 30 to about 51 grams per square meter, which is equivalent to a range of from about 0.8 to about 1.5 ounces per square yard.

The polypropylene meltblown fibers of which the nonwoven web is composed will have diameters in a range of from about 0.01 to about 50 micrometers. For example, the polypropylene meltblown fibers may have diameters in a range of from about 0.1 to about 10 micrometers. As another example, the polypropylene meltblown fibers may have diameters in a range of from about 15 to about 25 micrometers.

The nonwoven web is adapted to provide a sustained controlled release of an aqueous alcoholic composition contained within the web to a surface. The phrase "sustained controlled release" refers to at least three releases of the aqueous alcoholic composition to a surface in specified amounts. Thus, the first release of the aqueous alcoholic composition is in a range of from about 40 to about 60 weight percent of the composition originally present in the nonwoven web. The second release of the aqueous alcoholic composition is in a range of from about 12 to about 23 weight percent of the composition originally present in the nonwoven web. Finally, the third release of the aqueous alcoholic composition is in a range of from about 8 to about 18 weight percent of the composition originally present in the nonwoven web. The total amount of the aqueous alcoholic composition remaining in the nonwoven web after three releases will be no more than about 25 weight percent of the composition originally present.

When the polypropylene meltblown fibers have diameters in a range of from about 0.1 to about 10 micrometers, the aqueous alcoholic composition contained within the polypropylene nonwoven web may be present in a range of from about 500 to about 600 weight percent, based on a dry weight of the nonwoven web of 34 grams per square meter. Furthermore, the first release of the aqueous alcoholic composition may be in a range of from about 40 to about 55 weight percent of the composition originally present in the nonwoven web. The second release of the aqueous alcoholic composition may be in a range of from about 18 to about 23 weight percent of the composition originally present in the nonwoven web. The third release of the aqueous alcoholic composition may be in a range of from about 12 to about 18 weight percent of the composition in the nonwoven web. The total amount of the aqueous alcoholic composition remaining in the nonwoven web after three releases will be no more than about 25 weight percent of the composition originally present.

As stated earlier, the present invention also provides a method of applying a sustained controlled release of an aqueous alcoholic composition to a surface. The method involves providing a pattern bonded polypropylene nonwoven web adapted to provide a sustained controlled release to a surface of an aqueous alcoholic composition contained within the nonwoven web, which nonwoven web has a basis weight of from about 17 to about 100 grams per square meter and comprises polypropylene meltblown fibers having diameters in a range of from about 0.01 to about 50 micrometers, followed by loading the nonwoven web with an aqueous alcoholic composition in an amount of from about 400 to about 600 weight percent, based on a dry weight of the nonwoven web of 34 grams per square meter. A surface is wiped with the loaded nonwoven web a first time to release from about 40 to about 60 weight percent of the aqueous alcoholic composition originally present in the nonwoven web. A surface is wiped a second time to release from about 12 to about 23 weight percent of the aqueous alcoholic composition originally present in the nonwoven web, and then a third time to release from about 8 to about 18 weight percent of the aqueous alcoholic composition originally present in the nonwoven web. The total amount of the aqueous alcoholic composition remaining in the nonwoven web after wiping a surface three times is no more than about 25 weight percent of the composition originally present.

In general, the surface may be, without limitation, any surface which is capable of being wiped. The surface may be, by way of example only, countertops, utensils, kitchen fixtures and equipment, cutting boards, bathroom fixtures, toilet seats, public telephone handsets, and skin.

The present invention is further described by the example which follows. Such example, however, is not to be construed as limiting in any way either the spirit or the scope of the present invention.

EXAMPLE

A variety of materials were employed. The materials employed were assigned a letter identification (ID) and are described in Table 1. In the table, basis weights for the Kimberly-Clark Corporation nonwoven webs are average values.

TABLE 1

Summary of Samples Employed

| ID | Description |
|---|---|
| A | Paper Towels, Hi-Count basic 2-ply (Kimberly-Clark Corporation) |
| B | Handi Wipes, bonded carded web (Chicopee) |
| C | Woven washcloths, 100% cotton (K-Mart Corporation) |
| D | Cotton squares, pressed quilted cotton (Treasury Drug) |
| E | Sponge pads, Snap'N Shine wax applicator (Libman Co.) |
| F | Microwave cleaner pads, needled and saturated (Cadie Products Corp.) |
| G | 1.5 osy (about 51 gsm) polypropylene spunbond nonwoven web, RHT bonded, untreated (Kimberly-Clark Corporation) |
| H | 1.0 osy (about 34 gsm) polypropylene coarse meltblown nonwoven web, ERHT bonded, untreated (Kimberly-Clark Corporation) |
| I | 1.1 osy (about 37 gsm) polypropylene meltblown nonwoven web, ERHT bonded, untreated (Kimberly-Clark Corporation) |
| J | 1.1 osy (about 37 gsm) polypropylene meltblown nonwoven web, ERHT bonded, treated* (Kimberly-Clark Corporation) |
| K | 1.1 osy (about 37 gsm) polypropylene meltblown nonwoven web, unbonded, treated* (Kimberly-Clark Corporation) |

*Topically treated with Triton® X-102 (about 0.6 percent by weight add-on), an octylphenoxypolyethoxyethanol (Rohm & Haas).

The materials in Table 1 were cut into 3.5-inch by 4-inch (approximately 9-cm by 10-cm) samples. Each sample was saturated with an aqueous alcoholic composition containing 70 percent by volume isopropanol by simply immersing the sample in the composition. The sample was removed from the composition and held in a vertical position until dripping stopped. The sample then was weighed to determine the amount of the composition contained within the sample (pick-up). Pick-up was expressed as a percent based on the dry weight of the sample, as follows:

% Pick-up=100[(wet weight−dry weight)/dry weight]

Each sample was placed on a bench top made of quarried stone impregnated with a resin finish (Imperial Stone, Hamilton Industries) and covered with a wooden block four inches (about 10 cm) long cut from a piece of standard 2-inch by 4-inch (about 5-cm by 10-cm) lumber. A 4-kg weight was placed on the block and the weighted block was pulled by a string attached to the block a distance of five feet (about 1.5 meters) along the bench top at a rate of 1.5 feet per second (about 46 cm per second). The sample was reweighed, and the foregoing procedure was repeated two additional times. The results are summarized in Table 2.

TABLE 2

Summary of Release-To-Surface Testing Results

| ID | Basis Weight | Initial % Pick-up | % 1st Release | % 2nd Release | % 3rd Release | % Total Release |
|---|---|---|---|---|---|---|
| A | 1.0 (34) | 393 | 73 | 7 | 6 | 86 |
| B | 1.3 (44) | 400 | 61 | 14 | 9 | 84 |
| C | 8.7 (295) | 294 | 21 | 15 | 9 | 45 |
| D | 3.8 (129) | 563 | 34 | 21 | 12 | 66 |
| E | 4.6 (156) | 484 | 16 | 12 | 11 | 39 |
| F | 4.2 (142) | 1127 | 38 | 24 | 16 | 78 |
| G | 1.3 (44) | 429 | 67 | 11 | 7 | 86 |
| H | 1.0 (34) | 485 | 59 | 14 | 9 | 82 |
| I | 1.0 (34) | 589 | 42 | 21 | 13 | 76 |
| J | 0.9 (31) | 538 | 48 | 18 | 15 | 81 |
| K | 1,1 (37) | 546 | 33 | 18 | 16 | 66 |

*In ounces per square yard (grams per square meter).

In order to provide a basis for comparison, all of the values in Table 2 were normalized by dividing each value by the basis weight of the sample. These normalized values are summarized in Table 3.

TABLE 3

Normalized Release-To-Surface Testing Results
(Results per Unit Basis Weight)

| ID | Basis Weight | Initial % Pick-up | % 1st Release | % 2nd Release | % 3rd Release | % Total Release |
|---|---|---|---|---|---|---|
| A | 1.0 (34) | 393 | 73 | 7 | 6 | 86 |
| B | 1.0 (34) | 308 | 47 | 11 | 7 | 65 |
| C | 1.0 (34) | 34 | 2 | 2 | 1 | 5 |
| D | 1.0 (34) | 148 | 9 | 6 | 3 | 17 |
| E | 1.0 (34) | 105 | 4 | 3 | 2 | 8 |
| F | 1.0 (34) | 268 | 9 | 6 | 4 | 19 |
| G | 1.0 (34) | 330 | 52 | 8 | 5 | 66 |
| H | 1.0 (34) | 485 | 59 | 14 | 9 | 82 |
| I | 1.0 (34) | 589 | 42 | 21 | 13 | 76 |
| J | 1.0 (34) | 598 | 53 | 20 | 17 | 90 |
| K | 1.0 (34) | 496 | 30 | 16 | 15 | 60 |

*Normalized to 1 ounce per square yard (34 grams per square meter).

The data summarized in Table 3 clearly illustrate the present invention and the advantages resulting from the use thereof. Of all of the samples tested, only bonded meltblown webs meet the requirements specified herein. While the meltblown webs may have surfactant on the the surfaces of the fibers of which the webs are composed, surfactant is not required.

While the specification has been described in detail with respect to specific embodiments thereof, it will be appreciated by those skilled in the art, upon attaining an understanding of the foregoing, may readily conceive of alterations to, variations of, and equivalents to these embodiments. Accordingly, the scope of the present invention should be assessed as that of the appended claims and any equivalents thereto. For example, the wet wipe of the present invention may be packaged singly in a sealed container. Alternatively, a plurality of the wet wipes of the present invention may be packaged in a container adapted to keep the wipes in a saturated condition. The plurality of wipes may be interleaved, if desired. Other variations and equivalents will be apparent to those having ordinary skill in the art.

What is claimed is:

1. A wet wipe comprising:

a pattern bonded polypropylene nonwoven web adapted to provide a sustained controlled release of an aqueous alcoholic composition contained within the nonwoven web to a surface, which nonwoven web has a basis weight of from about 17 to about 100 grams per square meter and comprises polypropylene meltblown fibers having diameters in a range of from about 0.01 to about 50 micrometers;

wherein:

the aqueous alcoholic composition contained within the polypropylene nonwoven web is present in a range of from about 400 to about 600 weight percent, based on a dry weight of the nonwoven web of 34 grams per square meter;

the controlled release of the aqueous alcoholic composition contained within the web during use of the wipe being characterized by a first release of the aqueous alcoholic composition is in a range of from about 40 to about 60 weight percent of the composition originally present in the nonwoven web;

a second release of the aqueous alcoholic composition is in a range of from about 12 to about 23 weight percent of the composition originally present in the nonwoven web;

a third release of the aqueous alcoholic composition is in a range of from about 8 to about 18 weight percent of the composition originally present in the nonwoven web; and the total amount of the aqueous alcoholic composition remaining in the nonwoven web after three releases is no more than about 25 weight percent of the composition originally present.

2. The wet wipe of claim 1, in which the polypropylene meltblown fibers have diameters in a range of from about 0.1 to about 10 micrometers.

3. The wet wipe of claim 1, in which the polypropylene meltblown fibers have diameters in a range of from about 15 to about 25 micrometers.

4. The wet wipe of claim 1, in which the aqueous alcoholic composition is an aqueous ethanol composition.

5. The wet wipe of claim 1, in which the aqueous alcoholic composition is an aqueous propanol composition.

6. The wet wipe of claim 1, in which the aqueous alcoholic composition is an aqueous isopropanol composition.

7. A wet wipe comprising:

a pattern bonded polypropylene nonwoven web adapted to provide a sustained controlled release of an aqueous alcoholic composition contained within the nonwoven web to a surface, which nonwoven web has a basis weight of from about 17 to about 100 grams per square meter and comprises polypropylene meltblown fibers having diameters in a range of from about 0.1 to about 10 micrometers;

wherein:

the aqueous alcoholic composition contained within the polypropylene nonwoven web is present in a range of from about 500 to about 600 weight percent, based on a dry weight of the nonwoven web of 34 grams per square meter;

the controlled release of the aqueous alcoholic composition contained within the web during use of the wipe being characterized by a first release of the aqueous alcoholic composition is in a range of from about 40 to about 55 weight percent of the composition originally present in the nonwoven web;

a second release of the aqueous alcoholic composition is in a range of from about 18 to about 23 weight percent of the composition originally present in the nonwoven web;

a third release of the aqueous alcoholic composition is in a range of from about 12 to about 18 weight percent of the composition in the nonwoven web; and the total amount of the aqueous alcoholic composition remaining in the nonwoven web after three releases is no more than about 25 weight percent of the composition originally present.

8. The wet wipe of claim 7, in which the aqueous alcoholic composition is an aqueous ethanol composition.

9. The wet wipe of claim 7, in which the aqueous alcoholic composition is an aqueous propanol composition.

10. The wet wipe of claim 7, in which the aqueous alcoholic composition is an aqueous isopropanol composition.

11. A method of applying a sustained controlled release of an aqueous alcoholic composition to a surface, the method comprising:

providing a pattern bonded polypropylene nonwoven web adapted to provide a sustained controlled release to a surface of an aqueous alcoholic composition contained within the nonwoven web, which nonwoven web has a basis weight of from about 17 to about 100 grams per square meter and comprises polypropylene meltblown fibers having diameters in a range of from about 0.01 to about 50 micrometers;

loading the nonwoven web with an aqueous alcoholic composition in an amount of from about 400 to about 600 weight percent, based on a dry weight of the nonwoven web of 34 grams per square meter;

wiping a surface a first time to release from about 40 to about 60 weight percent of the aqueous alcoholic composition originally present in the nonwoven web;

wiping a surface a second time to release from about 12 to about 23 weight percent of the aqueous alcoholic composition originally present in the nonwoven web; and wiping a surface a third time to release from about 8 to about 18 weight percent of the aqueous alcoholic composition originally present in the nonwoven web; wherein the total amount of the aqueous alcoholic composition remaining in the nonwoven web after wiping a surface three times is no more than about 25 weight percent of the composition originally present.

12. The method of claim 11, in which the polypropylene meltblown fibers have diameters in a range of from about 0.1 to about 10 micrometers.

13. The method of claim 11, in which the polypropylene meltblown fibers have diameters in a range of from about 15 to about 25 micrometers.

14. The method of claim 11, in which the aqueous alcoholic composition is an aqueous ethanol composition.

15. The method of claim 11, in which the aqueous alcoholic composition is an aqueous propanol composition.

16. The method of claim 11, in which the aqueous alcoholic composition is an aqueous isopropanol composition.

* * * * *

UNITED STATES PATENT AND TRADEMARK OFFICE
CERTIFICATION OF CORRECTION

PATENT NO. : 5,656,361

DATED : August 12, 1997

INVENTOR(S): Clifford M. Vogt, Bernard Cohen, Clifford J. Ellis

It is certified that error appears in the above-identified patent and that said Letters Patent is hereby corrected as shown below:

Column 3, line 40, "carded" should read --carried--

Signed and Sealed this

Twenty-third Day of December, 1997

Attest:

BRUCE LEHMAN

*Attesting Officer*          *Commissioner of Patents and Trademarks*